United States Patent [19]

Zeugner et al.

[11] Patent Number: 4,533,662

[45] Date of Patent: * Aug. 6, 1985

[54] 2-ACYLAMINOMETHYL-1,4-BENZODIAZEPINE COMPOUNDS AND ANALGESIC USE

[75] Inventors: Horst Zeugner, Hanover, Fed. Rep. of Germany; Dietmar Roemer, Allschwil, Switzerland; Hans Liepmann, Hanover; Wolfgang Milkowski, Burgdorf, both of Fed. Rep. of Germany

[73] Assignee: Kali-Chemie Pharma GmbH, Hanover, Fed. Rep. of Germany

[*] Notice: The portion of the term of this patent subsequent to Apr. 20, 1999 has been disclaimed.

[21] Appl. No.: 330,324

[22] Filed: Dec. 14, 1981

[30] Foreign Application Priority Data

Dec. 20, 1980 [DE] Fed. Rep. of Germany ....... 3048264

[51] Int. Cl.$^3$ ................. A61K 31/55; C07D 243/16; C07D 405/10
[52] U.S. Cl. ................. 514/221; 260/239 BD; 260/330.9
[58] Field of Search ............ 260/239 BD, 330.9; 424/244, 278, 282

[56] References Cited

U.S. PATENT DOCUMENTS 3,998,809 12/1976 Milkowski et al. .......... 260/239 BD
4,096,141 6/1978 Milkowski et al. .......... 260/239 BD
4,325,957 4/1982 Zeugner et al. ............ 260/239 BD

FOREIGN PATENT DOCUMENTS 2436147 2/1975 Fed. Rep. of Germany ...... 260/239 BD

OTHER PUBLICATIONS

Burger, Medicinal Chemistry, (Second Edition, New York, 1960), pp. 79–81.
Wagner et al., Synthetic Organic Chemistry, (New York, 1953), pp. 566–569.

Primary Examiner—Alton D. Rollins

Attorney, Agent, or Firm—Schwartz, Jeffery, Schwaab, Mack, Blumenthal & Evans

[57] ABSTRACT

Novel 2-acyl amino methyl-5-phenyl-1H-2,3-dihydro-1,4-benzo diazepine compounds of the following Formula I

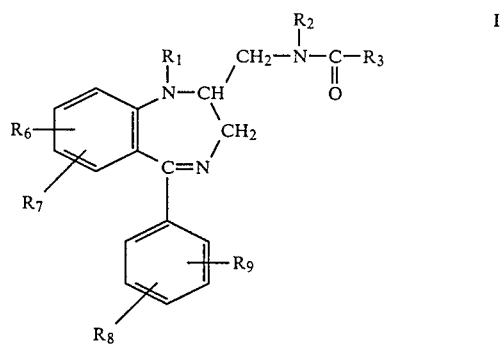

which have valuable pharmacological properties are provided. In said Formula I the acyl group —CO—$R_3$ represents a benzoyl group or a phenyl alkanoyl group which may be unsubstituted or mono- or di-substituted in the phenyl ring. The substituent $R_1$ in said compounds indicates lower alkyl, lower alkenyl, or cyclopropyl methyl, and the substituent $R_2$ indicates hydrogen, lower alkyl, or lower alkenyl, while the substituent $R_6$ indicates hydrogen, halogen, lower alkyl, lower alkoxy, hydroxyl, lower alkylthio, nitro, trifluoro methyl, cyano, amino, mono- or di-lower alkyl amino, lower mono-alkanoyl amino, lower N-alkyl-N-alkanoyl amino, or lower alkanoyloxy, and the substituent $R_7$ indicates hydrogen, halogen, lower alkyl, lower alkoxy, hydroxyl, or lower alkanoyloxy, whereby $R_6$ and $R_7$, when attached to adjacent carbon atoms, may form together the methylene dioxy or the ethylene dioxy group. The substituents $R_8$ and $R_9$ designate the same substituents as indicated for the substituents $R_6$ and $R_7$.

The compounds of Formula I have a surprising analgesic activity.

28 Claims, No Drawings

2-ACYLAMINOMETHYL-1,4-BENZODIAZEPINE COMPOUNDS AND ANALGESIC USE

BACKGROUND OF THE INVENTION (1) Field of the Invention

The present invention relates to novel 2-phenyl acyl amino methyl-5-phenyl-1,4-benzo diazepine compounds and their acid addition salts, to processes of making said compounds, to pharmaceutical compositions containing said compounds, and to methods of using such compositions in therapy.

(2) Description of the Prior Art

5-Phenyl-1,4-benzo diazepine compounds which are substituted in 2-position by a substituted methyl group, among them 2-acyl amino methyl-5-phenyl-1,4-benzo diazepine compounds, in which the acyl group is a low molecular alkanoyl group or a trimethoxy benzoyl group, are disclosed in U.S. Pat. Nos. 3,998,809 and 4,096,141. Said compounds exhibit mainly central nervous system depressing and anticonvulsive activities.

SUMMARY OF THE INVENTION

It is one object of the present invention to provide novel and highly advantageous 2-acyl amino methyl-1,4-benzo diazepine compounds which exhibit a novel profile of pharmacological activity which differs from those of the known compounds.

Another object of the present invention is to provide advantageous processes for producing such compounds.

A further object of the present invention is to provide novel and highly effective pharmaceutical compositions containing such compounds.

Still another object of the present invention is to provide a method of using said compounds and pharmaceutical compositions containing same in therapy.

Other objects of the present invention and advantageous features thereof will become apparent as the description proceeds.

Surprisingly it has been found that the novel 2-phenyl acyl amino methyl-5-phenyl-1,4-benzo diazepine compounds according to the present invention have a pronounced analgesic activity in addition to their sedative, diuretic, and antiarrhythmic properties and are of low toxicity.

In principle, the present invention relates to 2-phenyl acyl amino methyl-1H-2,3-dihydro-1,4-benzo diazepine compounds of the following formula I

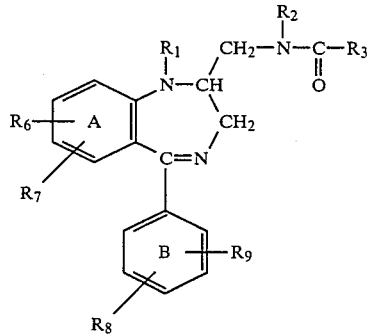

In said Formula I $R_1$ indicates hydrogen, lower alkyl, lower alkenyl, or cyclopropyl methyl, $R_2$ indicates hydrogen, lower alkyl, or lower alkenyl, $R_3$ indicates a group of the formula

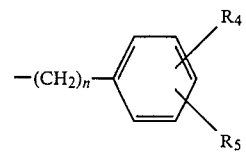

in which $R_4$ indicates hydrogen, halogen, lower alkyl, lower alkoxy, hydroxyl, lower alkylthio, nitro, trifluoro methyl, cyano, amino, lower mono- or di-alkyl amino, lower mono-alkanoyl amino, lower N-alkyl-N-alkanoyl amino, or lower alkanoyloxy, and $R_5$ indicates hydrogen, halogen, lower alkyl, lower alkoxy, hydroxyl, or lower alkanoyloxy, or $R_4$ and $R_5$, when attached to adjacent carbon atoms, together indicate the methylene di-oxy group or the ethylene di-oxy group, n indicates one of the numerals 0, 1, or 2, $R_6$ indicates hydrogen, halogen, lower alkyl, lower alkoxy, hydroxyl, lower alkylthio, nitro, trifluoro methyl, cyano, amino, lower mono- or di-alkyl amino, lower mono-alkanoyl amino, lower N-alkyl-N-alkanoyl amino, or lower alkanoyloxy, $R_7$ indicates hydrogen, halogen, lower alkyl, lower alkoxy, hydroxyl, or lower alkanoyloxy, or $R_6$ and $R_7$, when attached to adjacent carbon atoms, together indicate methylene di-oxy or ethylene di-oxy, $R_8$ indicates hydrogen, lower alkyl, lower alkoxy, hydroxyl, lower alkylthio, nitro, trifluoro methyl, cyano, amino, lower mono- or di-alkyl amino, lower mono-alkanoyl amino, lower N-alkyl-N-alkanoyl amino, or lower alkanoyloxy, $R_9$ indicates hydrogen, halogen, lower alkyl, lower alkoxy, hydroxyl, or lower alkanoyloxy, or $R_8$ and $R_9$, when attached to adjacent carbon atoms, together indicate methylene di-oxy or ethylene di-oxy.

The present invention also relates to the optically active isomers of said compounds and to their acid addition salts.

Suitable alkyl or alkenyl radicals $R_1$ and $R_2$ are low molecular alkyl or alkenyl radicals with up to 4 carbon atoms, which may be of straight chain or branched structure, for instance, methyl, ethyl, propyl, isopropyl, n-butyl, 1-methyl propyl, 2-methyl propyl, tertiary butyl, allyl, 2-butenyl, or 3-butenyl. More particularly the substituent $R_1$ is hydrogen, lower alkyl, or cyclopropyl methyl, and preferably lower alkyl, especially methyl. The substituent $R_2$ is preferably hydrogen.

If in the compounds of Formula I the substituents $R_4$ and $R_5$, the substituents $R_6$ and $R_7$ of the phenylene ring A, or the substituents $R_8$ and $R_9$ of the phenyl ring B represent lower alkyl groups or contain such lower alkyl groups, said groups can be straight chain or branched lower alkyl groups and preferably contain 1 to 4 carbon atoms. Said substituents are more particularly the methyl, ethyl, n-propyl, isopropyl, n-butyl, 1-methyl propyl, 2-methyl propyl, or tertiary butyl and preferably methyl, ethyl, n-propyl, and isopropyl. If the phenyl rings are disubstituted, ethyl and preferably methyl are preferred. Preferred low molecular alkoxy or alkylthio substituents are the methoxy or the methylthio groups.

If the substituents $R_4$ to $R_9$ are halogen atoms, fluorine, chlorine, or bromine are especially useful. If a phenyl ring is substituted by alkylthio, nitro, trifluoromethyl, cyano, amino, or substituted amino groups, mono-substitution is preferred.

The 2-phenyl acyl amino methyl-1H-2,3-dihydro-1,4-benzo diazepine compounds of Formula I as well as their optically active isomers and their acid addition salts are produced according to the present invention by acylating in a manner known per se 2-amino methyl-1H-2,3-dihydro-1,4-benzo diazepine compounds of Formula II

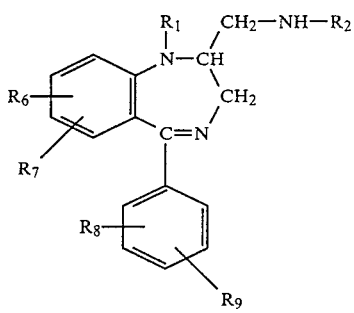

or their acid addition salts with a carboxylic acid or a reactive carboxylic acid derivative of Formula III

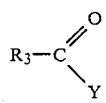

in an inert solvent at a temperature between $-30°$ C. and the boiling point of the solvent used. In said starting materials of Formula II the substituents $R_1$, $R_2$, $R_6$, $R_7$, $R_8$, and $R_9$ indicate the same substituents as given hereinabove with respect to the compounds of Formula I. In the carboxylic acid or reactive carboxylic acid derivative of Formula III the substituent $R_3$ has the same meaning as indicated hereinabove with respect to the benzo diazepine compounds of Formula I, while Y indicates hydroxyl, halogen, lower alkoxy, or an O—CO—Z group, in which Z indicates the substituent $R_3$ or lower alkoxy.

If desired, the resulting compounds of Formula I in which $R_2$ indicates hydrogen, can be alkylated to yield compounds of Formula I in which $R_2$ indicates lower alkyl or lower akenyl. Likewise in compounds of Formula I in which $R_6$ and/or $R_7$ indicate hydrogen, there can be introduced chlorine, bromine, the hydroxyl group, or the nitro group into the phenyl ring. Or in compounds of Formula I in which the substituents $R_4$, $R_5$, $R_6$, $R_7$, $R_8$, and/or $R_9$ indicate lower alkanoyloxy or lower alkanoyl amino groups, these groups can be hydrolyzed to hydroxy or amino.

If desired, the resulting racemic mixtures of compounds of Formula I can be resolved into their optically active isomers. One may convert the free bases of Formula I into the corresponding acid addition salts. Likewise the acid addition salts may be converted into the corresponding free bases of Formula I.

Acylation of the amino methyl compounds of Formula II can be carried out by methods conventionally used for forming acid amide groups by amino acylation. Amino acylation can take place in a solvent which is inert under the reaction conditions, at temperatures between $-30°$ C. and the boiling point of the solvent and under atmospheric or increased pressure. Suitable solvents are halogenated hydrocarbons such as methylene chloride or chloroform, aromatic hydrocarbons such as benzene, toluene, xylene, chloro benzene, cyclic ethers such as tetrahydrofurane, dioxane, ketones such as acetone, methyl isobutyl ketone, or dimethyl formamide. Mixtures of said solvents can, of course, also be used.

When using carboxylic acid halogenides or carboxylic acid anhydrides of Formula III as acylating agents, the reaction is preferably carried out in the presence of an acid binding agent. Suitable agents capable of combining with and binding acids are, for instance, inorganic bases, such as potassium carbonate, sodium carbonate, or potassium hydroxide, or organic bases, more particularly tertiary lower alkyl amines, such as triethyl amine, tripropyl amine, or tributyl amine, or pyridines, such as pyridine, 4-dimethyl amino pyridine, or 4-pyrrolidino pyridine. When added in excess to the reaction mixture, the tertiary amines can additionally serve as inert solvents.

When using, as the one reactant, a compound of Formula III, in which Y indicates the substituent halogen, those compounds, in which the substituent Y is chlorine, are the most preferred reactants.

When using, as the one reactant, a compound of Formula III, in which the substituent Y indicates a low molecular alkoxy group, the reaction is preferably carried out in a closed reaction vessel. In this case the ester may be added in excess, thus serving as solvent. The reaction can be catalytically effected by the addition of a metal alcoholate, for instance, by the addition of aluminum isopropylate or aluminum tri-alkylcompounds.

If the acid itself or an ester thereof is used as acylating agent, the reaction of the amino compound of Formula II with the acid of Formula III or with its ester, is most advantageously carried out in the presence of a suitable coupling agent. Coupling agents which favorably affect formation of acid amides are generally known, for instance, from the peptide chemistry. More particularly N-lower alkyl-2-halogeno pyridinium salts and especially their halogenides or tosylates may be mentioned as examples of such coupling agents which promote acid amide formation by reacting with the acid in situ, thereby producing a reactive acid derivative. Preferred coupling agents of this type are, for instance N-methyl-2-chloro pyridinium iodide (described, for instance by Mukaiyama in "Angewandte Chemie" Vol. 91 (1979), pages 789–812) and alkyl carbodi-imides and especially cycloalkyl carbodi-imides, preferably dicyclohexyl carbodi-imide or carbonyl di-imidazole. The reaction in the presence of a coupling agent can be carried out more expediently at a temperature between about $-30°$ C. and about $+30°$ C. in the presence of an inert organic solvent, such as halogenated hydrocarbons and/or aromatic hydrocarbons. An acid binding amine may also be present. Other suitable coupling agents as they are also used in peptide syntheses, which are suitable for the acid amide synthesis according to the present invention, are known, for instance, from the book by Jerry March entitled "Advanced Organic Chemistry", published by McGraw-Hill Ltd., 2nd edition, pages 382–388, and from the book by Jacob Zabicky entitled "The Chemistry of Amides" published by Interscience Publishers John Wiley and Sons, London, 1970, Chapter 2 on the "Synthesis of Amides".

If in compounds of Formula III the substituents $R_4$ and/or $R_5$ are amino groups, monosubstituted amino groups, or hydroxyl groups, said groups can be provided with a protecting group before they are used in the reaction. Said protecting group can be split off after the reaction is completed. If required, the protecting group can be split off by hydrolysis. The free amino groups, mono-alkyl amino groups, or hydroxyl groups can be protected before the reaction in an especially advantageous manner by conversion into sulfinyl imino groups, acetyl alkyl amino groups, or acetoxy groups respectively which can readily be split up after reaction.

Resulting compounds of Formula I, in which $R_2$ indicates hydrogen, can subsequently be converted into the corresponding N-alkyl compounds. For instance, compounds of Formula I in which the substituent $R_2$ indicates hydrogen, can be converted subsequently into the corresponding organo-metal compounds by reaction with an agent capable of metalating the compound, such as sodium hydride, lithium butyl, lithium phenyl, sodium amide, lithium di-isopropyl amide, sodium alkoxide, or thallium (I) alkoxide. The metalating reaction is carried out in the presence of a suitable inert solvent. Thereupon, the resulting metalated compound is alkylated by reaction with an alkylating agent, for instance, with an alkyl halogenide, an alkyl sulfate, or an alkyl sulfonic acid ester, at a temperature between $-80°$ C. and the boiling point of the solvent used.

The inert solvents used are, of course, dependent on the agent selected for metalating the compound of Formula I.

Suitable solvents are, for instance, diethyl ether, tetrahydrofurane, dioxane, benzene, toluene, dimethyl formamide, or dimethyl sulfoxide. Solvents for the metal alkoxides are also the corresponding alcohols, such as, when using metal methoxides, methanol, or, when using metal ethoxides, ethanol.

The compounds of Formula I according to the present invention are obtained in the form of their racemates, when using for their synthesis racemic compounds of Formula II. The present invention, of course, comprises not only the racemic mixtures of the compounds of Formula I, but also their optically active isomers. Said racemic mixtures of the compounds of Formula I can be separated into their optically active isomers in a manner known per se by the formation of salts with suitable optically active acids, such as, for instance, tartaric acid, O,O'-dibenzoyl tartaric acid, mandelic acid, di-O-isopropylidene-2-oxo-L-gulonic acid, and the like. Subsequently the optically active antipodes are recovered by fractional crystallization of the resulting salts (see S. H. Willen, A. Collet, and J. Jacques "Tetrahedron" Vol. 33 (1977), pages 2725–2736). The free optically active bases can be produced from said optically active salts. Said bases can be converted, if desired, into their pharmacologically compatible acid addition salts. The racemic mixtures and their optically active isomers and also their acid addition salts can be purified by recrystallization from suitable solvents, such as lower alcohols and/or ethers.

Separation into optically active compounds can also be effected in a suitable preliminary step of producing the starting material of Formula II.

The 2-amino methyl compounds of Formula II used as starting compounds are known. Their preparation can be effected in a manner known per se, for instance, according to the process described in U.S. Pat. Nos. 3,998,809 and 4,096,141.

Preferably an acyl diamine of Formula IV

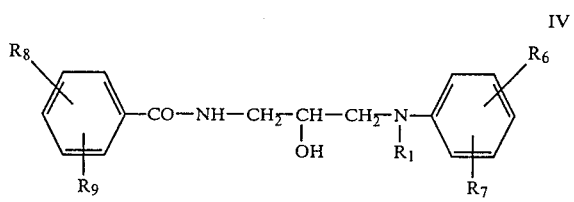

in which $R_1$, $R_6$, $R_7$, $R_8$, and $R_9$ indicate the same substituents as given hereinabove, is heated under reflux with an excess of phosphorus oxychloride for several hours. Thereupon, the resulting mixture of isomers consisting of compounds of Formula V and VI

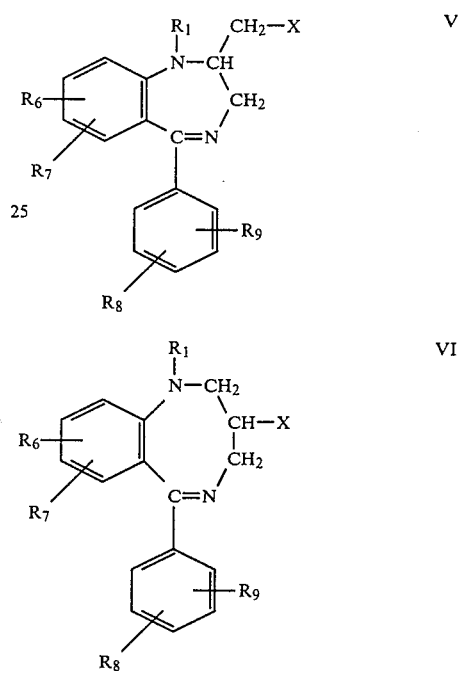

in which $R_1$, $R_6$, $R_7$, $R_8$, and $R_9$ indicate the same substituents as given hereinabove, while X indicates chlorine, is separated from the reaction mixture. The 2-amino methyl-1,4-benzo diazepine compounds of Formula II are obtained from the mixture containing compounds of Formula V and VI by reaction with ammonia or primary amines, optionally in the presence of suitable solvents at temperatures between 20° C. and 150° C. and under atmospheric pressure or under increased pressure. In some instances it can be of advantage to first convert the mixture of the isomers of Formulas V and VI in a manner known per se by reaction with an alkali metal imide and preferably with potassium phthalimide, into the corresponding 2-imido methyl-1,4-benzo diazepine derivatives, for instance, into the corresponding 2-phthalimido methyl-1,4-benzo diazepine. Or the mixture may first be racted with an alkali metal azide, preferably with sodium or potassium azide to yield the corresponding 2-azido methyl-1,4-benzo diazepine derivative. Both compounds, the 2-amido methyl- and the 2-azido methyl-1,4-benzo diazepine compounds can then be transformed in a manner known per se into the corresponding 2-amino methyl-1,4-benzo diazepine compounds of Formula II.

A subsequent substitution in the phenyl ring of the 1,4-benzo diazepine ring system by halogen or the nitro group can be effected at the stage of the cyclisised intermediate products as well as with the final products in a manner known per se. Thereby, the reaction is carried out according to the methods described in the above mentioned U.S. Patents.

Suitable halogenating agents are, for instance, N-chloro succinimide or N-bromo succinimide. The nitro group can be introduced by means of the usual nitrating agents, for instance, by means of potassium nitrate in sulfuric acid or by means of copper$^{II}$ nitrate trihydrate in acetic acid anhydride as a mildly acting nitrating agent.

Starting compounds of Formula II in which the substituent $R_1$ is hydrogen, can also be obtained by dealkylating compounds of Formula II in which $R_1$ is alkyl and preferably methyl, by reaction with hydrogen iodide in a manner known per se, provided, of course, that the benzo diazepine ring system of the starting compounds does not contain alkoxy groups and/or alkylthio groups as substituents. The reaction can be carried out at a temperature between 50° C. and 100° C. in concentrated hydrogen iodide.

The compounds of Formula I as they are obtained by the process according to the present invention are isolated either in the form of the free bases or they are converted, if desired, in a manner known per se into their acid addition salts with inorganic or organic acids. For this purpose, the desired acid serving as salt forming component is added, for instance, to a solution of the compound of Formula I in a suitable solvent. Advantageously organic solvents in which the resulting acid addition salt is insoluble, are selected for the salt forming reaction, so that the salt can readily be separated by filtration. Suitable solvents are, for instance, ethanol, isopropanol, ether, acetone, acetic acid ethyl ester, mixtures of acetone and ether, of acetone and ethanol, or of ethanol and ether.

It is known from the literature that 1,4-benzo diazepine compounds which are substituted in 2-position possess valuable pharmacological properties. More particularly the known 1,4-benzo diazepine compounds are effective in the central nervous system (see the above mentioned U.S. Patents.

On account of their anxiolytic and aggression suppressing properties they have proved to be valuable drugs for the treatment of said symptoms in humans. It is surprising that the novel 2-phenyl acyl amino methyl-1,4-benzo diazepine compounds according to the present invention exhibit a new kind of profile of pharmacological activity whereby, in addition to psychopharmacological, diuretic, and anti-arrhythmic properties, pronounced analgesic properties predominate. Thus the compounds of Formula I exhibit in pharmacological tests with animals an analgesic activity within a dosage range of 0.1 mg./kg. and 100 mg./kg.

The compounds according to the present invention are highly advantageous, useful, and effective analgesic agents on account of their pronounced analgesic activity.

It can be shown by pharmacological tests with small rodents and with monkeys that the compounds of Formula I according to the present invention are capable of increasing the pain threshold value in mammals. This effect can be proved more particularly by two pharmacological test methods, the tail flick test with mice and the arthritis pain test with rats.

DESCRIPTION OF THE PHARMACOLOGICAL TEST METHODS

1. Determination of the minimum toxic dose.

Maximum doses of 300 mg./kg. of the compound to be tested are administered per os to male mice of a weight of 20 g. to 25 g. The animals are carefully observed for any toxicity symptoms during 3 hours. In addition thereto all symptoms and deaths are registered for a period of time of 24 hours after administration of the drug. Any accompanying symptoms are also observed and registered. When death or toxic symptoms are observed, more and more decreasing doses are administered to other mice, until no more toxic symptoms are encountered. The lowest dose which causes toxic symptoms is given as the minimum toxic dose.

2. Arthritis pain test with rats.

Male rats of the strain OFA weighing 160 g. to 180 g. are anesthesized by intraperitoneal administration of 20 mg./kg. of pentobarbital sodium. 0.1 ml. of suspension of Mycobacterium Smegmae (S I043) in paraffin oil (0.6 mg. of Mycobacterium in 0.1 ml. of paraffin oil) are injected intracutaneously into the left hind paw. Fourteen days thereafter, when a pronounced secondary arthritis has developed particularly in the right hind paw, the effects of the compound to be tested are investigated. 30 minutes before the administration of the compound to be tested, a control measurement is carried out by bending three times the ankle joint of the right hind paw and the number of squeaks produced by the animal are counted. Rats which do not react are eliminated. Three hours after oral administration of the compound to be tested, the bending procedure is repeated. Animals which emit only one squeak or none at all, are considered to be protected against pain. Between 9 and 20 rats are tested per dose and the $ED_{50}$ (95% confidence limit) is determined according to the method of Litchfield and Wilcoxon (1949). The dose which achieves protection in 50% of the treated animals is designated as the $ED_{50}$.

3. Tail flick test with mice.

The method is based on the procedure described by d'Amour and Smith in 1941. In contrast thereto there are used, in place of rats, fed male and female mice of a body weight of 16 g. to 25 g. 30 minutes before treatment with the compound to be tested each mouse is placed into a separate cylindrical container of such a size that the mouse cannot turn around and cannot move forward. Its tail extends outwardly of the container while resting in a narrow trough. A specific spot of the tail of each animal (at a distance of about 35 mm. from the tail root) is exposed to the heat of radiation of a lamp of known strength and temperature. The lamp is positioned directly underneath the tail. The time in seconds which the mouse needs in order to jerk the tail out of the range of the light ray, is determined twice, once 30 minutes and another time 15 minutes before the subcutaneous administration of the compound (10 mg./kg) to be tested. Mice, the reaction time of which deviates by more than 25%, are eliminated and disregarded. The reaction times are again measured 15 minutes and 30 minutes after administration. An increase in the reaction times by more than 75% of the average reaction time values measured before administration of the test compound to the same mouse is considered an analgesic effect. The dose which causes the reaction time, measured 30 minutes after administration of the test compound, to be 75% longer in 50% of the animals than the reaction time measured before administration, is considered as ED$_{50}$ (95% confidence limit) of each tested compound. The ED$_{50}$ is calculated according to the method of Litchfield and Wilcoxon (1949).

In the following table there are given results which were obtained by proceeding according to the above described test methods. The example numbers given in said table for various compounds of Formula I refer to the compounds as they are described hereinafter in more detail in the working examples.

| Compd. of Formula I accordg. to Example No. | Suppression of arthritis pain in rats ED$_{50}$ mg./kg. p.o. | Tail flick test in mice ED$_{50}$ mg./kg. s.c. | Minimum toxic dose in mice mg./kg. p.o. |
|---|---|---|---|
| 18 | 7.5 | | >300 |
| 19 | ~2.3 | 1.0 | >300 |
| 20 | ~4 | 4.6 | 300 |
| 25 | 3.2 | 2.5 | |
| 28 | 0.6 | | >300 |
| 29 | 1.7 | 21 | 300 |
| 31 | <18>10 | 1.8 | >300 |
| 32 | 1.7 | 4.2 | 300 |
| 33 | <10>5,6 | 1.4 | >300 |
| 35 | 9 | 13 | |
| 40 | 11 | | >300 |
| 1 | 19 | 0.52 | >300 |
| 2 | 2.0 | 0.64 | 50 |
| 4 | 0.5 | 0.07 | 10 |
| 47 | ~13 | 5.6 | >300 |
| 49 | 2.5 | 0.56 | 100 |
| 55 | <18>10 | >5.6<10 | |
| 58 | ~18 | 1.6 | 300 |
| 59 | 9.7 | 1 | 300 |
| 60 | 3.5 | 0.32 | 300 |
| 112 | 10 | 20 | 50 |
| 113 | <32>18 | <5.6 | 100 |
| 117 | 6 | 13 | >300 |
| 154 | 2 | | |
| 155 | ~2 | | |

The free bases as well as their pharmaceutically acceptable acid addition salts can be used as medicaments. Said acid addition salts are salts with such acids, the anions of which are substantially nontoxic at the dosages administered. It is furthermore of advantage that the salts to be used as medicaments are well crystallizable and only slightly or not at all hygroscopic. The following acids are, for instance, especially suitable for forming acid addition salts with compounds of Formula I: Hydrochloric acid, hydrobromic acid, sulfuric acid, phosphoric acid, methane sulfonic acid, ethane sulfonic acid, benzene sulfonic acid, p-toluene sulfonic acid, citric acid, lactic acid, acetic acid, succinic acid, maleic acid, fumaric acid, tartaric acid, malic acid, benzoic acid, phenyl acetic acid, and mandelic acid.

The compounds of Formula I can be administered in the form of suitable pharmaceutical formulations for treating and relieving pain. For this purpose the dose is to be adjusted with respect to the type of species to be treated and to the individual requirements. In general, pain relieving effects are achieved in test animals with doses between 0.1 mg./kg. and 100 mg./kg. To achieve pain relief in humans and larger mammals there have proved to be of value, for instance, compositions containing 0.25–50 mg. preferably 1–50 mg. of the active compound in each single dose. Formulations which are to be administered parenterally contain, in general, less of the active compound than perorally administered preparations.

The compounds of Formula I can be used as such or in combination with pharmaceutically applicable carrier materials or excipients and with conventional pharmaceutical adjuvants in many dosage forms. For instance, solid preparations such as tablets, capsules, powders, granulates, suppositories, dragees, and the like can be prepared for administration. Solid preparations can contain an inorganic carrier material or excipient such as talcum, or an organic carrier material or excipient, such as starch or lactose. Other additions of conventional adjuvants, such as lubricants, for instance, magnesium stearate may also be admixed. Fluid preparations such as solutions, suspensions, or emulsions can contain the conventional diluents, such as water, paraffins, suspending agents, such as poly-oxy ethylene glycols, and the like. Furthermore, other components may also abe added, such as preservatives, stabilizing agents, and wetting agents.

DESCRIPTION OF THE PREFERRED EMBODIMENTS

The following examples serve to illustrate the present invention and more particularly the preparation of the novel compounds of Formula I without, however, being limited thereto.

The composition and strucure of the resulting novel compounds are ascertained by spectroscopic investigations especially by an exact analysis of the NMR spectra. The amide-C=O-band is determined in the infrared spectrum within the range of 1630–1650 cm$^{-1}$. The composition, salts, and melting points of the novel compounds are given in the table of examples. In this table any enclosed amounts of water, acetone, ethanol, or the like which are incorporated in the respective acid addition salts, are listed.

EXAMPLE 1

1-Methyl-2-benzoyl amino methyl-5-phenyl-1H-2,3-dihydro-1,4-benzo diazepine (a) 50.5 g. of N$_1$-benzoyl-N$_2$-methyl-N$_2$-phenyl-2-hydroxy-1,3-diamino propane are boiled under reflux with 250 ml. of phosphorus oxychloride for 2½ hours. Afer working up the reaction mixture in a manner known per se, 48 g. of a mixture of 1-methyl-2-chloro methyl-5-phenyl-1H-2,3-dihydro-1,4-benzo diazepine and 1-methyl-3-chloro-6-phenyl-1,2,3,4-tetrahydrobenzodiazocine are obtained as residue. Said mixture is boiled with 34.6 g. of potassium phthalimide and 9.6 g. of potassium iodide in 350 ml. of methanol for 22 hours. Thereby 64.1 g. of 1-methyl-2-phthalimido methyl-5-phenyl-1H-2,3-dihydro-1,4-benzo diazepine are obtained. Without further purification said compound is heated under reflux with 17.8 g. of hydrazine hydrate in 800 ml. of ethanol. The resulting 1-methyl-2-amino methyl-5-phenyl-1H-2,3-dihydro-1,4-benzo diazepine is converted in the usual manner into its di-hydrochloride of the melting point 209°–213° C.

(b) 19.3 g. of the above mentioned di-hydrochloride are dissolved in 260 ml. of methylene chloride. 26 ml. of tri-ethyl amine are added to said solution. A solution of 7.3 ml. of benzoyl chloride in 40 ml. of methylene chloride is added drop by drop thereto while cooling the reaction mixture with ice. The solution is then stirred at room temperature for 2 more hours and is washed first with 100 ml. of water, then with 100 ml. of a 20% ammonia solution, followed by washing with 50 ml. of water and twice, each time with 50 ml. of a saturated sodium chloride solution. The organic phase is dried over anhydrous sodium sulfate and is filtered. The resulting filtrate is freed from its solvent by distillation in a vacuum. 16.3 g. of the crude base as given hereinabove are obtained as residue. Said base is dissolved in ether and an ethereal solution of hydrochloric acid is added thereto. The precipitated hydrochloride crystals are filtered off and are stirred several times with hot acetone. 8.4 g. of 1-methyl-2-benzoyl amino methyl-5-phenyl-1H-2,3-dihydro-1,4-benzo diazepine di-hydrochloride are obtained in the form of yellow crystals of the melting point: 217°–218° C.

EXAMPLE 2

8-Methoxy-1-methyl-2-benzoyl amino methyl-5-(4'-fluoro phenyl)-1H-2,3-dihydro-1,4-benzo diazepine 10.0 g. of 8-methoxy-1-methyl-2-amino methyl-5-(4'-fluoro phenyl)-1H-2,3-dihydro-1,4-benzo diazepine are dissolved in 200 ml. of methylene chloride and 5.26 ml. of tri-ethyl amine are added thereto. Thereupon a solution of 3.8 ml. of benzoylchloride in 50 ml. of methylene chloride is added drop by drop at a temperature of −5° C. On working up the reaction mixture, there are obtained 6.8 g. of 8-methoxy-1-methyl-2-benzoyl amino methyl-5-(4'-fluoro phenyl)-1H-2,3-dihydro-1,4-benzo diazepine di-hydrochloride containing 0.8 moles of water. Its melting point is 219°–222° C.

EXAMPLE 3

7-Bromo-1-methyl-2-(3-amino benzoyl amino methyl)-5-(2'-chloro phenyl)-1H-2,3-dihydro-1,4-benzo diazepine 14.4 g. of 7-bromo-1-methyl-2-amino methyl-5-(2'-chloro phenyl)-1H-2,3-dihydro-1,4-benzo diazepine are dissolved in 200 ml. of methylene chloride and 6.1 ml. of tri-ethyl amine are added thereto. Thereupon a solution of 8.5 g. of 3-sulfinyl imino benzoyl chloride in 50 ml. of methylene chloride is added drop by drop thereto while cooling with ice. The 3-sulfinyl imino benzoyl chloride is obtained by reaction of thionyl chloride with 3-amino benzoic acid. The reaction mixture is then stirred at room temperature overnight. The resulting methylene chloride phase is then worked up by extracting it by shaking with dilute 12% hydrochloric acid. The base is then set free by the addition of 50% sodium hydroxide solution, and is extracted with methylene chloride. 17.1 g. of the crude base, identified hereinabove, are obtained on working up the methylene chloride extract in a manner known per se. Preliminary purification of said base is effected by conversion of the base into its di-hydrochloride. After reconversion of said salt into the base, whereby 8.5 g. thereof are obtained, the base is further purified by thin layer chromatography over silica gel by means of an eluting agent consisting of chloroform, ethanol, and concentrated ammonia solution in the proportion of 90:5:1 parts by volume. The di-hydrochloride produced from the thus purified base in a yield of 4.0 g. contains 1 mole of ethanol and 1 mole of water per mole of salt and has a melting point of 231°–235° C.

EXAMPLE 4

8-Methoxy-1-methyl-2-benzoyl amino methyl-5-(2',4'-dichloro phenyl)-1H-2,3-dihydro-1,4-benzo diazepine 12.8 g. of benzoic acid are dissolved in 300 ml. of methylene chloride. The resulting solution is cooled to a temperature between 0° C. and 5° C. 24.6 ml. of tri-ethyl amine are added thereto. Thereupon 10 ml. of chloro formic acid ethyl ester are added drop by drop thereto within about 5 to 10 minutes. The reaction solution is then stirred at a temperature between 0° C. and 5° C. for 30 more minutes and is then added drop by drop, while cooling and excluding moisture, to a solution of 38.2 g. of 8-methoxy-1-methyl-2-amino methyl-5-(2',4'-dichloro phenyl)-1H-2,3-dihydro-1,4-benzo diazepine in 200 ml. of methylene chloride in such a manner that the temperature is kept between 0° C. and 5' C. The reaction solution is then stirred at room temperature for 4 more hours. After working up the reaction solution, there are obtained 50.3 g. of the crude above identified base which is converted into its hydrochloride of a melting point of 246°–248° C. Yield: 35.5 g.

EXAMPLE 5

1-Methyl-2-(3-methoxy benzoyl amino methyl)-5-phenyl-1H-2,3-dihydro-1,4-benzo diazepine 9.19 g. of 2-chloro-1-methyl pyridinium iodide are suspended in 300 ml. of methylene chloride at room temperature and under exclusion of moisture, while stirring. 10 ml. of tri-ethyl amine and 4.56 g. of 3-methoxy benzoic acid are added thereto. After 15 minutes there is added drop by drop a solution of 7.7 g. of 1-methyl-2-amino methyl-5-phenyl-1H-2,3-dihydro-1,4-benzo diazepine in 100 ml. of methylene chloride within 15 minutes. After stirring for 30 more minutes there are admixed thereto 300 ml. of water and such a small amount of an aqueous ammonia solution that the reaction mixture is adjusted to slightly ammoniacal reaction. 12.5 g. of an oily residue are obtained from the methylene chloride phase. Said residue is chromatographically purified over 150 g. of technical grade silica gel by successive elution with ether, methylene chloride, and ethanol. The hydrochloride obtained from the resulting, above identified base, is recrystallized from isopropanol. The thus purified hydrochloride has a melting point of 205°–210° C. The yield amounts to 10.8 g.

EXAMPLE 6

1-Methyl-2-(2-hydroxy benzoyl amino methyl)-5-phenyl-1H-2,3-dihydro-1,4-benzo diazepine 1-Methyl-2-[(2-acetoxy benzoyl)amino methyl]-5-phenyl-1H-2,3-dihydro-1,4-benzo diazepine is produced from 15 g. of 1-methyl-2-amino methyl-5-phenyl-1H-2,3-dihydro-1,4-benzo diazepine and 10 g. of acetyl salicylic acid in accordance with the procedure as described in Example 5. The resulting reaction product is saponified to the above identified compound of saponification with a 20% solution of sodium hydroxide in methanol within 30 minutes. The crude product obtained as an oily residue by extraction with methylene chloride, is dissolved in isopropanol and is converted into its hydrochloride by introduction of hydrogen chloride. The resulting hydrochloride is precipitated by the addition of ether. On recrystallization from a mixture of isopropanol and methanol, there are recovered 12.2 g. of the hydrochloride of the melting point 221–224° C.

EXAMPLE 7

7-Bromo-1-methyl-2-(2-fluoro benzoyl amino methyl)-5-(2'-fluoro phenyl)-1H-2,3-dihydro-1,4-benzo diazepine A mixture of 1-methyl-2-chloro methyl-5-(2'-fluoro phenyl)-1H-2,3-dihydro-1,4-benzo diazepine and 1-methyl-3-chloro-6-(2'-fluoro phenyl)-1,2,3,4-tetrahydrobenzodiazocine is produced by cyclization of $N_1$-(2-fluoro benzoyl)-$N_2$-methyl-$N_2$-phenyl-2-hydroxy-1,3-diamino propane by means of phosphorus oxychloride. 30.3 g. of said mixture in 300 ml. of methylene chloride are boiled under reflux with 17.8 g. of N-bromo succinimide for 24 hours. The brominated reaction product is reacted in a manner known per se with potassium phthalimide in methanol to yield 1-methyl-2-phthalimido methyl-7-bromo-5-(2'-fluoro phenyl)-1H-2,3-dihydro-1,4-benzo diazepine. After cleavage of said compound by means of hydrazine hydrate, there are obtained 17.3 g. of 7-bromo-1-methyl-2-amino methyl-5-(2'-fluoro phenyl)-1H-2,3-dihydro-1,4-benzo diazepine. Said compound is dissolved in 250 ml. of methylene chloride together with 6.7 ml. of tri-ethyl amine. The resulting solution is reacted with 7.6 g. of 2-fluoro benzoyl chloride. After working up the reaction mixture in a manner known per se, the resulting base as identified hereinabove is converted into its hydrochloride of the melting point 238°–242° C.

Yield: 12.3 g.

EXAMPLE 8

2-Benzoyl amino methyl-5-phenyl-1H-2,3-dihydro-1,4-benzo diazepine 10 g. of 1-methyl-2-amino methyl-5-phenyl-1H-2,3-dihydro-1,4-benzo diazepine are heated in 40 ml. of 67% hydrogen iodide at 80° C. for 4 hours, while stirring. Thereupon the reaction solution is neutralized by means of solid sodium carbonate, with the addition of 500 g. of ice. After addition of 50 ml. of concentrated sodium hydroxide solution, the mixture is extracted with methylene chloride. Working up of the resulting methylene chloride phase in the usual manner yields 9.0 g. of 2-amino methyl-5-phenyl-1H-2,3-dihydro-1,4-benzo diazepine in the form of an oil. Said compound is dissolved in 150 ml. of methylene chloride together with 4.2 ml. of tri-ethyl amine. The resulting solution is reacted with 4.2 g. of benzoyl chloride. 7.1 g. of 2-benzoyl amino methyl-5-phenyl-1H-2,3-dihydro-1,4-benzo diazepine are obtained in the from of an oily crude product. The pure compound is isolated by recrystallization from a mixture of methylene chloride and ether as base. 0,005 HCl, FP 168°–169° C.

EXAMPLE 9

7-Nitro-1-methyl-2-benzoyl amino methyl-5-phenyl-1H-2,3-dihydro-1,4-benzo diazepine To a solution of 11.1 g. of 1-methyl-2-chloro methyl-5-phenyl-1H-2,3-dihydro-1,4-benzo diazepine in 100 ml. of glacial acetic acid there are added 30 ml. of concentrated sulfuric acid. Thereafter a solution of 9.6 g. of potassium nitrate in 21 ml. of concentrated sulfuric acid is added at a temperature of 5° C. Stirring of the reaction mixture is continued for one more hour. The mixture is then poured on ice, dilute sodium hydroxide solution is added, and the mixture is extracted with chloroform. On working up the extract in the usual manner, there are obtained 4.3 g. of 7-nitro-2-chloro methyl-5-phenyl-1H-2,3-dihydro-1,4-benzo diazepine. The melting point of its hydrochloride is 212°–215° C. By reacting said compound with potassium phthalimide and splitting up the resulting reaction product by means of 24% hydrochloric acid, it is converted into 7-nitro-1-methyl-2-amino methyl-5-phenyl-1-H,2,3-dihydro-1,4-benzo diazepine.

Said compound is reacted with benzoylchloride and trie-ethyl amine in methylene chloride solution. On working up the reaction mixture, there are obtained 1.1 g. of 7-nitro-1-methyl-2-benzoyl amino methyl-5-phenyl-1H-2,3-dihydro-1,4-benzo diazepine in the form of an oil. Said oil is converted into its hydrochloride which has a melting point of 212°–215° C.

EXAMPLE 10

1-Methyl-2-[benzoyl-(N-methyl)-amino methyl]-5-phenyl-1H-2,3-dihydro-1,4-benzo diazepine 9.3 g. of 1-methyl-2-benzoyl amino methyl-5-phenyl-1H-2,3-dihydro-1,4-benzo diazepine are dissolved in 100 ml. of tetrahydrofurane. 0.75 g. of sodium hydride in the form of an 80% solution in paraffin oil are added to the resulting solution of the benzo diazepine compound in tetrahydrofurane at room temperature, while stirring. Thereupon a solution of 1.55 ml. of methyl iodide in 10 ml. of tetrahydrofurane is slowly added drop by drop at 5° C. to the reaction mixture. The resulting mixture is stirred at 5° C. to 10° C. for 2 hours and is then worked up in a manner known per se after the addition of toluene and ice water. 7.2 g. of 1-methyl-2-[benzoyl-(-methyl)amino methyl]-5-phenyl-1H-2,3-dihydro-1,4-benzo diazepine are obtained in the form of an oily base.

EXAMPLE 11

1-Methyl-2-(2-chloro phenacetyl amino methyl)-5-phenyl-1H-2,3-dihydro-1,4-benzo diazepine To a mixture of 33.8 g. of 1-methyl-2-amino methyl-5-phenyl-1H-2,3-dihydro-1,4-benzo diazepine di-hydrochloride and 25.1 g. of tri-ethyl amine in 460 ml. of methylene chloride there is added drop by drop a solution of 23.3 g. of 2-chloro phenacetyl chloride in 140 ml. of methylene chloride while cooling with ice. Thereafter the reaction mixture is stirred at room temperature for one more hour. After working up the reaction mixture in the usual manner with ice and water, there are obtained 54.2 g. of the crude compound as designated hereinabove. Said compound is purified by means of 200 ml. of ether and 50 g. of γ-alumina. The purified base yields 17.5 g. of 1-methyl-2-(2-chloro phenacetyl amino methyl)-5-phenyl-1H-2,3-dihydro-1,4-benzo diazepine hydrochloride of the melting point 163°–164.5° C.

EXAMPLE 12

1-Methyl-2-(3-phenyl propionyl amino methyl)-5-phenyl-1H-2,3-dihydro-1,4-benzo diazepine 14.5 g. of 3-phenyl propionic acid are dissolved in 250 ml. of methylene chloride and 14.5 ml. of tri-ethyl amine are added thereto. To the resulting mixture there are added drop by drop 10 ml. of chloro formic acid ethyl ester, while cooling with ice so as to maintain an internal temperature of 2° C. to 5° C. Thereupon the reaction solution is stirred at said temperature for 30 more minutes. A solution of 26.5 g. of 1-methyl-2-amino methyl-5-phenyl-1H-2,3-dihydro-1,4-benzo diazepine in 200 ml. of methylene chloride is added to the solution of 3-phenyl propionic acid and tri-ethyl amine in such a manner that the temperature is maintained between 0° C. and 5° C. After stirring the reaction mixture at room temperature for 4 more hours, it is worked up in the usual manner. 21.5 g. of 1-methyl-2-(3-phenyl propional amino methyl)-5-phenyl-1H-2,3-dihydro-1,4-benzo diazepine are obtained in the form of an oily base. Said base is converted into its hydrochloride salt which crystallizes. The salt is composed of 1 mole base, 1.8 moles hydrochloric acid, and 0.5 mole water. Its melting point is 112°–114° C.

EXAMPLE 13

1-Methyl-2-benzoyl amino methyl-5-phenyl-1H-2,3-dihydro-1,4-benzo diazepine 26.5 g. of 1-methyl-2-amino methyl-5-phenyl-1H-2,3-dihydro-1,4-benzo diazepine are heated with an excess of benzoic acid methyl ester (100 ml.) to 120° C. for 2 hours. Thereupon excess ester and the methanol formed during the reaction are slowly distilled off in a vacuum. A residue in the amount of 36 g. of crude reaction product is obtained thereby. On working up the same in the usual manner and converting it into its hydrochloride, there are obtained 24.7 g. of 1-methyl-2-benzoyl amino methyl-5-phenyl-1H-2,3-dihydro-1,4-benzo diazepine hydrochloride. Its melting point is 217°–218° C.

EXAMPLE 14

1-Methyl-2-[benzoyl-(N-n-propyl)amino methyl]-5-phenyl-1H-2,3-dihydro-1,4-benzo diazepine 15.4 g. of 1-methyl-2-(N-n-propyl)amino methyl-5-phenyl-1H-2,3-dihydro-1,4-benzo diazepine are dissolved in 250 ml. of ether. 2.8 g. of quinuclidine are added to said solution. To the resulting mixture there are added drop by drop 7.1 g. of benzoyl chloride dissolved in 100 ml. of ether, while cooling with ice. As soon as the benzoyl chloride has been added, the resulting reaction mixture is worked up in the usual manner. 11.2 g. of 1-methyl-2-[benzoyl-(N-n-propyl)amino methyl]-5-phenyl-1H-2,3-dihydro-1,4-benzo diazepine are obtained in the form of the oily base.

By proceeding as described in the foregoing examples 1 to 14, there can be produced the following compounds of Formula I in which the substituents $R_1$, $R_2$, $R_4$, $R_5$, n, $R_6$, $R_7$, $R_8$, and $R_9$ indicate the substituents given in the following table. The compounds are obtained by acylation of correspondingly substituted 2-amino methyl-5-phenyl-1H-2,3-dihydro-1,4-benzo diazepine compounds with correspondingly substituted acylating compounds of Formula III:

| Example No. | $R_1$ | $R_2$ | Substitution in Ring A | | Substitution in Ring B | | n | $R_4$ | $R_5$ | Acid addition salt | M.P. °C. |
|---|---|---|---|---|---|---|---|---|---|---|---|
| | | | $R_6$ | $R_7$ | $R_8$ | $R_9$ | | | | | |
| 15 | $CH_3$ | H | H | H | H | H | 0 | 2-Cl | H | HCl | 195–197 |
| 16 | $CH_3$ | H | H | H | H | H | 0 | 2-F | H | HCl | 189–193 |
| 17 | $CH_3$ | H | H | H | H | H | 0 | 2-$OCH_3$ | H | HCl | 196–199 |
| 18 | $CH_3$ | H | H | H | H | H | 0 | 2,4-di-Cl | | HCl | 254–260 |
| 19 | $CH_3$ | H | H | H | H | H | 0 | 3,4-di-Cl | | HCl | 172–175 |
| 20 | $CH_3$ | H | H | H | H | H | 0 | 4-$OCH_3$ | H | HCl | 215–220 |
| 21 | $CH_3$ | H | H | H | H | H | 0 | 4-$CF_3$ | H | p-tos. | 169–174 |
| 22 | $CH_3$ | H | H | H | H | H | 0 | 4-OH | H | HCl | 260–265 |
| 23 | $CH_3$ | H | H | H | H | H | 0 | 3,4-di-$OCH_3$ | | HCl | 214–218 |
| 24 | $CH_3$ | H | H | H | H | H | 0 | 3,5-di-$OCH_3$ | | HCl | 215–217 |
| 25 | $CH_3$ | H | H | H | H | H | 0 | 4-$CH_3$ | H | HCl | 195–199 |
| 26 | $CH_3$ | H | H | H | H | H | 0 | 3-$CH_3$ | H | HCl | 199–201 |
| 27 | $CH_3$ | H | H | H | H | H | 0 | 2-$CH_3$ | H | HCl | 189–193 |
| 28 | $CH_3$ | H | H | H | H | H | 0 | 4-$NO_2$ | H | HCl | 216–220 |
| 29 | $CH_3$ | H | H | H | 2-F | H | 0 | 4-CN | H | HCl | 239–242 |
| 30 | $CH_3$ | H | H | H | 2-F | H | 0 | 2-$OCH_3$ | H | HCl.0.2 $H_2O$.0.1 i-$C_3H_7OH$ | 213–216 |
| 31 | $CH_3$ | H | H | H | 2-F | H | 0 | 3-$OCH_3$ | H | HCl | 225–228 |
| 32 | $CH_3$ | H | H | H | 2-F | H | 0 | 4-$OCH_3$ | H | HCl.0,4 i-$C_3H_7OH$ | 201–205 |
| 33 | $CH_3$ | H | H | H | 2-F | H | 0 | 4-$CF_3$ | H | HCl | 184–188 |
| 34 | $CH_3$ | H | H | H | 2-F | H | 0 | 4-OH | H | HCl | 253–257 |
| 35 | $CH_3$ | H | H | H | 2-F | H | 0 | 3-CN | H | HCl | 185–188 |
| 36 | $CH_3$ | H | 8-$CH_3$ | H | 4-F | H | 0 | 4-$OCH_3$ | H | HCl | 255–259 |
| 37 | $CH_3$ | H | H | H | 2-F | H | 0 | 3-OH | H | Base | 200–201 |
| 38 | $CH_3$ | H | H | H | 2-F | H | 0 | 3,4-O—$CH_2$—O | | HCl | 190–192 |
| 39 | $CH_3$ | H | H | H | 4-F | H | 0 | 2-$OCH_3$ | H | HCl | 175–181 |
| 40 | $CH_3$ | H | H | H | 4-F | H | 0 | 4-$OCH_3$ | H | HCl | 147–154 |
| 41 | $CH_3$ | H | H | H | 4-F | H | 0 | 2-$CH_3$ | H | HCl | 125–128 |
| 42 | $CH_3$ | H | H | H | 4-F | H | 0 | 3-$CH_3$ | H | HCl | 199–203 |
| 43 | $CH_3$ | H | H | H | 4-F | H | 0 | 4-$CH_3$ | H | Base | 77–83 |
| 44 | $CH_3$ | H | H | H | H | H | 0 | 4-$OC_2H_5$ | H | 1,05 HCl | 196–201 |
| 45 | $CH_3$ | H | H | H | 2-F | H | 0 | 2-OH | H | HCl | 219–223 |
| 46 | $CH_3$ | H | 7-$CH_3$ | H | 2-F | H | 0 | 3,4-di-Cl | | HCl | 220–225 |
| 47 | $CH_3$ | H | 7-$CH_3$ | H | 2-F | H | 0 | H | H | HCl | 249–254 |
| 48 | $CH_3$ | H | 8-$OCH_3$ | H | 4-F | H | 0 | 2-Cl | H | HCl | 236–239 |
| 49 | $CH_3$ | H | 7,8-O—$CH_2$—O | | H | H | 0 | H | H | HCl | 253–262 |
| 50 | $CH_3$ | H | 7,8-O—$CH_2$—O | | H | H | 0 | 2-Cl | H | HCl | 246–253 |
| 51 | $CH_3$ | H | 7,8-O—$C_2H_5$—O | | H | H | 0 | 3,4-di-Cl | | HCl | 263–266 |
| 52 | $CH_3$ | H | 7,8-O—$C_2H_5$—O | | H | H | 0 | H | H | HCl | 267–274 |
| 53 | $CH_3$ | H | 7-$OCH_3$ | H | H | H | 0 | H | H | HCl | 252–257 |
| 54 | $CH_3$ | H | 8-$OCH_3$ | H | 4-$CF_3$ | H | 0 | H | H | HCl | 239–241 |
| 55 | $CH_3$ | H | 8-$OCH_3$ | H | 3-$CF_3$ | H | 0 | H | H | HCl | 211–213 |
| 56 | $CH_3$ | H | 8-$OCH_3$ | H | 2-F | H | 0 | 3,4-di-Cl | | HCl | 202–203 |

-continued

| Example No. | $R_1$ | $R_2$ | Substitution in Ring A $R_6$ | $R_7$ | Substitution in Ring B $R_8$ | $R_9$ | n | $R_4$ | $R_5$ | Acid addition salt | M.P. °C. |
|---|---|---|---|---|---|---|---|---|---|---|---|
| 57 | $CH_3$ | H | 8-$OCH_3$ | H | 3-F | H | 0 | 3,4-di-Cl | | HCl | 215–217 |
| 58 | $CH_3$ | H | 8-$OCH_3$ | H | 3-F | H | 0 | H | H | HCl | 200–232 (Z) |
| 59 | $CH_3$ | H | 8-F | H | H | H | 0 | H | H | HCl | 214–217 |
| 60 | $CH_3$ | H | 8-$OCH_3$ | H | 2-F | H | 0 | H | H | HCl | 216–219 |
| 61 | $CH_3$ | H | H | H | 2-F | H | 1 | 2-F | H | Base | 146–147 |
| 62 | $CH_3$ | H | 7-Br | H | 2-Cl | H | 0 | 3-F | H | HCl | 243–245 |
| 63 | $CH_3$ | H | 7-Br | H | 2-Cl | H | 0 | 2-F | H | HCl | 215–217.5 |
| 64 | $CH_3$ | H | 7-Br | H | 2-Cl | H | 0 | 3,4-O—$CH_2$—O | | HCl | 250–251 |
| 65 | $CH_3$ | H | 7-Br | H | 2-Cl | H | 0 | 3,4-di-$OCH_3$ | | HCl | 237–239 |
| 66 | $CH_3$ | H | 7,8-di-$OCH_3$ | | 3,4-di-$OCH_3$ | | 0 | 2-F | H | HCl.$H_2O$ | 167–170 |
| 67 | $CH_3$ | H | 7-Br | H | 2-Cl | H | 0 | 4-F | H | HCl | 226–229 |
| 68 | $CH_3$ | H | 7-Br | H | 2-Cl | H | 0 | 2-Cl | H | HCl | 205–208 |
| 69 | $CH_3$ | H | H | H | 2-F | H | 0 | 2,4-di-Cl | | HCl | 180–185 |
| 70 | $CH_3$ | H | H | H | 4-F | H | 0 | 4-F | H | HCl | 182–187 |
| 71 | $CH_3$ | H | 8-F | H | 2-F | H | 0 | H | H | HCl | 191–194 |
| 72 | $CH_3$ | H | 7-F | 8-$CH_3$ | H | H | 0 | H | H | HCl | 112–116 |
| 73 | $CH_3$ | H | 7-$CH_3$ | 8-F | H | H | 0 | H | H | HCl | 233–237 |
| 74 | $CH_3$ | H | H | H | 4-Br | H | 0 | 4-C($CH_3$)$_3$ | H | Base | 174–175 |
| 75 | $CH_3$ | H | H | H | 4-Br | H | 0 | H | H | Base | 168–171 |
| 76 | $CH_3$ | H | H | H | 4-F | H | 0 | 3-$OCH_3$ | H | HCl | 199–204 |
| 77 | $CH_3$ | H | H | H | 4-F | H | 0 | 4-OH | H | 1,25 HCL.0,65 $C_2H_5OH$ | 184–189 |
| 78 | $CH_3$ | H | H | H | 4-Br | H | 0 | 3,5-di-$CH_3$ | | | |
| 79 | $CH_3$ | H | 8-$CH_3$ | H | 2-F | H | 0 | H | H | Base | O |
| 80 | $CH_3$ | H | 8-$CH_3$ | H | 4-F | H | 0 | H | H | Base.1 $H_2O$ | 91–93 |
| 81 | $CH_3$ | H | 8-$CH_3$ | H | 4-F | H | 0 | 4-$CH_3$ | H | Base.1 $H_2O$ | 93–96 |
| 82 | $CH_3$ | H | 8-$CH_3$ | H | 2-$CH_3$ | H | 0 | H | H | HCl | 231–235 |
| 83 | $CH_3$ | H | H | H | 2-F | H | 0 | 3-F | 6-$NH_2$ | Base | O |
| 84 | $CH_3$ | H | H | H | 2-F | H | 0 | 4-$NH_2$ | H | HCl | 115–119 |
| 85 | $CH_3$ | H | H | H | 4-F | H | 0 | 4-$NHCOCH_3$ | H | Base | 122–126 |
| 86 | $CH_3$ | H | H | H | 4-F | H | 0 | 4-$NHCH_3$ | H | HCl | 165–170 |
| 87 | $CH_3$ | H | H | H | 4-F | H | 0 | 4-N($CH_3$)$_2$ | H | HCl | 162–166 |
| 88 | $CH_3$ | H | 8-$CH_3$ | H | 2,4-di-Cl | | 0 | H | H | HCl | 252–256 |
| 89 | $CH_3$ | H | H | H | 4-$CH_3$ | H | 0 | 4-F | H | HCl | 206–210 |
| 90 | $CH_3$ | H | 8-$OCH_3$ | H | 2-F | H | 0 | 4-$CH_3$ | H | HCl | 160–162 |
| 91 | $CH_3$ | H | 8-$OCH_3$ | H | 2-F | H | 0 | H | H | p-tos | 182–183 |
| 92 | $CH_3$ | H | 8-$OCH_3$ | H | 4-Br | H | 0 | H | H | HCl | 239–241 |
| 93 | $CH_3$ | H | H | H | 2,4-di-$CH_3$ | | 0 | H | H | HCl | 195–197 |
| 94 | $CH_3$ | H | H | H | 4-OH | H | 0 | 4-OH | H | HCl | 105–109 |
| 95 | n-$C_4H_9$ | H | 8-Br | H | 4-$OCH_3$ | H | 0 | 4-$NO_2$ | H | Base | O |
| 96 | n-$C_4H_9$ | H | 8-Br | H | 4-F | H | 0 | 4-$NO_2$ | H | HCl | 197–200 |
| 97 | $CH_3$ | H | 7-$CH_3$ | H | 4-F | H | 0 | H | H | HCl | 194–197 |
| 98 | $CH_3$ | H | 7-$CH_3$ | H | 4-F | H | 0 | 4-$OCH_3$ | H | HCl | 208–211 |
| 99 | $CH_3$ | H | 7-$CH_3$ | H | 2-F | H | 1 | H | H | Base | O |
| 100 | $CH_3$ | H | 7-$CH_3$ | H | 2-$CH_3$ | H | 0 | H | H | Base | O |
| 101 | $CH_3$ | H | 7-$CH_3$ | H | H | H | 0 | H | H | Base | O |
| 102 | $CH_3$ | H | 8-$CH_3$ | H | H | H | 0 | H | H | HCl | 248–252 |
| 103 | $CH_3$ | H | H | H | H | H | 0 | 3-OH | 4-$CH_3$ | HCl | 173–178 |
| 104 | $CH_3$ | H | 8-$NO_2$ | H | H | H | 0 | 4-$CH_3$ | H | HCl | 241–245 |
| 105 | $CH_3$ | H | H | H | 2-F | 5-$NO_2$ | 0 | H | H | 1,2 HCl. 0,2 $H_2O$ | 119–123 |
| 106 | $CH_3$ | H | H | H | H | H | 0 | 2-$OCOCH_3$ | H | Base | O |
| 107 | $CH_3$ | H | 8-OH | H | H | H | 0 | 4-$CH_3$ | H | 1.15 HCl. 0,25 $C_2H_5OH$ | 127–131 |
| 108 | $CH_3$ | H | H | H | 2-Cl | 6-F | 0 | 4-CN | H | HCl | 236–250 (Z) |
| 109 | $CH_3$ | H | H | H | 2-$CH_3$ | H | 0 | 4-CN | H | HCl.0,35 ($CH_3$)$_2$CO. 0,15 $H_2O$ | 174–180 |
| 110 | $CH_3$ | H | H | H | H | H | 0 | 4-CN | H | HCl | 208–212 |
| 111 | $CH_3$ | H | 7-Cl | H | H | H | 1 | H | H | HCl | 218–220 |
| 112 | $CH_3$ | H | 7-Cl | H | H | H | 1 | 3,4-di-$OCH_3$ | | HCl | 192–195 |
| 113 | $CH_3$ | H | 7,8-O—$CH_2$—O | | H | H | 1 | 3,4-di-$OCH_3$ | | HCl | 178–180 |
| 114 | $CH_3$ | H | H | H | H | H | 1 | 4-Br | H | 1,15 HCl 0,3 $H_2O$ | 194–197 |
| 115 | $CH_3$ | H | H | H | H | H | 1 | 4-Cl | H | HCl.0,7 $H_2O$ | 98–102 |
| 116 | $CH_3$ | H | H | H | 4-Br | H | 1 | 4-Br | H | HCl.0,3 $H_2O$ | 179–182 |
| 117 | $CH_3$ | H | H | H | 2-F | H | 1 | 2-Cl | H | HCl | 171–174 |
| 118 | $CH_3$ | H | H | H | 4-F | H | 1 | 2-Cl | H | Base. 0,15 $H_2O$ | 143–145 |
| 119 | $CH_3$ | H | H | H | 2-F | H | 1 | 4-Cl | H | HCl. 0.6 $H_2O$ | 99–105 |
| 120 | $CH_3$ | H | H | H | 4-F | H | 1 | 3-Cl | H | Base | 141–145 |
| 121 | $CH_3$ | H | H | H | H | H | 1 | 4-Cl | H | HCl | 205–209 |
| 122 | $CH_3$ | H | H | H | 2-F | H | 1 | H | H | 0,875 HCl. 1 $H_2O$ | 107–122 |
| 123 | $CH_3$ | H | H | H | 2-F | H | 1 | 3-Cl | H | Base | 169–170 |

-continued

| Example No. | $R_1$ | $R_2$ | Substitution in Ring A $R_6$ | $R_7$ | Substitution in Ring B $R_8$ | $R_9$ | n | $R_4$ | $R_5$ | Acid addition salt | M.P. °C. |
|---|---|---|---|---|---|---|---|---|---|---|---|
| 124 | $CH_3$ | H | 7,8-di-$OCH_3$ | | H | H | 1 | 2-Cl | H | HCl | 211,5–212 |
| 125 | $CH_3$ | H | 7-Br | | 2-Cl | H | 1 | 3,4-O—$C_2H_2$—O | | HCl | 177–179 |
| 126 | $CH_3$ | H | 7-Br | | 2-Cl | H | 1 | 3,4-di-$OCH_3$ | | HCl | 190–191 |
| 127 | $CH_3$ | H | H | H | H | H | 1 | 3-Cl | H | 1,1 HCl. 0,6 $H_2O$ | 92–96 |
| 128 | $CH_3$ | H | H | H | 2-F | H | 1 | 2,4-di-Cl | | Base. 0,15 HCl | 109–112 |
| 129 | H | H | H | H | H | H | 1 | H | | Base | 0 |
| 130 | $CH_3$ | H | 8-F | H | 2-F | H | 1 | H | H | HCl | 88–90 |
| 131 | $CH_3$ | H | 7-F | 8-$CH_3$ | H | H | 1 | H | H | HCl. 0.4 $H_2O$ | 95–99 |
| 132 | $CH_3$ | H | 7-$CH_3$ | 8-F | H | H | 1 | H | H | HCl | 120–125 |
| 133 | $CH_3$ | H | 8-$CH_3$ | H | 2-F | H | 1 | H | H | Base | 151–154 |
| 134 | $CH_3$ | H | 8-$CH_3$ | H | 4-F | H | 1 | 4-$OCH_3$ | H | 1,1 HCl. 0,4 $H_2O$ | 110–115 |
| 135 | $CH_3$ | H | 8-$CH_3$ | H | 2,4-di-Cl | | 1 | H | H | HCl.0,5 $H_2O$ | 123–127 |
| 136 | $CH_3$ | H | 8-$OCH_3$ | H | 2-F | H | 1 | H | H | HCl.0,5 $H_2O$ | 113–117 |
| 137 | $CH_3$ | H | 8-$OCH_3$ | H | 2-F | H | 1 | 2-Cl | H | 1,55 HCl. 0,3 $H_2O$. 0,25 $(CH_3)_2CO$ | 123–128 |
| 138 | $C_2H_5$ | H | H | H | 2-F | H | 1 | 2-Cl | H | Base | 147–150 |
| 139 | $C_2H_5$ | H | H | H | 2-F | H | 1 | 2-F | H | Base | 90–96 |
| 140 | n-$C_4H_9$ | H | H | H | 2-F | H | 1 | 2-Cl | H | Base | 174–176 |
| 141 | n-$C_3H_7$ | H | H | H | 2-F | H | 1 | 2-Cl | H | Base | 167–172 |
| 142 | $CH_3$ | H | H | H | H | H | 1 | 4-$OCH_3$ | H | Base | 0 |
| 143 | $CH_3$ | H | H | H | 2-$CH_3$ | H | 1 | 2-Cl | H | HCl.0,1 $(CH_3)_2CO$. 0,05 $CH_3COOC_2H_5$. 0,25 $H_2O$ | 110–115 |
| 144 | $CH_3$ | H | H | H | 4-F | H | 2 | 4-OH | H | 1,75 HCl. 0,4 $H_2O$ | 125–128 |
| 145 | $CH_3$ | H | H | H | H | H | 2 | 4-OH | H | 1,9 HCl. 0,9 $H_2O$ | 136–139 |
| 146 | $CH_3$ | H | H | H | 2-F | H | 2 | H | H | 1,6 HCl. 1,2 $H_2O$ | 94–101 |
| 147 | $CH_3$ | H | 7-F | 8-$CH_3$ | H | H | 2 | H | H | Base | 0 |
| 148 | $CH_3$ | H | 7-$CH_3$ | 8-F | H | H | 2 | H | H | Base | 0 |
| 149 | $CH_3$ | H | 8-$CH_3$ | H | 2-F | H | 2 | H | H | Base. 0,1 $C_2H_5OH$ | 128–130 |
| 150 | $CH_3$ | H | 8-$OCH_3$ | H | 2-F | H | 2 | H | H | 1,65 HCl. 0,45 $H_2O$ | 112–116 |
| 151 | $CH_3$ | H | 8-$CH_3$ | H | 2-F | H | 2 | 4-$OCH_3$ | H | HCl. 0,39 $H_2O$ | 87–93 |
| 152 | n-$C_4H_9$ | H | H | H | 2-F | H | 0 | 4-$CF_3$ | H | HCl. 0,3 i-$C_3H_7OH$. 0,2 $H_2O$ | 128–131 |
| 153 | n-$C_4H_9$ | H | H | H | H | H | 0 | 4-$CF_3$ | H | HCl | 188–190 |
| 154 | $C_2H_5$ | H | H | H | 2-F | H | 0 | 4-$CF_3$ | H | p-tos. 0,1 $H_2O$. 0,4 i-$C_3H_7OH$ | 170–172 |
| 155 | $C_2H_5$ | H | H | H | H | H | 0 | 4-$CF_3$ | H | p-tos | 210–212 |
| 156 | $C_2H_5$ | H | H | H | 2-F | H | 0 | 2-OH | H | cyclam | 155–157 |
| 157 | $C_2H_5$ | H | H | H | H | H | 0 | 2-OH | H | HCl.0,05 i-$C_3H_7OH$. 0,1 $H_2O$ | 183–185 |
| 158 | $CH_3$ | $(CH_3)_2CH$ | H | H | H | H | 0 | 2-Cl | H | Base | 152–154 |
| 159 | $CH_3$ | H | 7-F | H | H | H | 0 | 4-CN | H | Base | 166–167 |
| 160 | $CH_3$ | H | 7-F | H | 2-F | H | 0 | 4-CN | H | Base | 146–148 |
| 161 | $CH_3$ | H | 7-F | H | 2-F | H | 1 | 3,4-di-$OCH_3$ | | Base | 75–81 |
| 162 | $CH_3$ | H | 8-$CH_3$ | H | 2-F | H | 1 | 3,4-di-$OCH_3$ | | Base | 118–121 |
| 163 | $CH_3$ | H | H | H | 2-Cl | H | 1 | 4-$OCH_3$ | H | HCl | 177–179 |
| 164 | $CH_3$ | H | 8-$CH_3$ | H | 4-$NO_2$ | H | 0 | 4-$OCH_3$ | H | HCl | 212–216 |
| 165 | $CH_3$ | H | 7-$CH_3$ | H | 4-F | H | 0 | 4-F | H | HCl | 225–227 | z = Decomposition
HCl = Hydrochloric acid
p-tos = p-Tosylate
Base = Free Base
Cyclam = Cyclamate The following examples serve to illustrate processes of preparing pharmaceutical compositions containing compounds of Formula I according to the present invention without, however, being limited thereto:

EXAMPLE I

Tablets

Tablets are prepared which contain the following components per tablet:

| | |
|---|---|
| 1-Methyl-2-(3,4-dichloro benzoyl amino methyl)-5-phenyl-1H—2,3-dihydro-1,4-benzo diazepine hydrochloride | 15 mg. |
| Corn starch | 60 mg. |
| Lactose | 140 mg. |
| Gelatine (10% solution) | 6 mg. |

The active compound, corn starch, and lactose are thickened with the 10% gelatine solution and the paste obtained thereby is triturated. The resulting granulated material is placed upon a suitable metal plate and is dried at a temperature of 45° C. The resulting dried granular material is conducted through a comminuting device. Then the following agents are admixed to the resulting powder in a mixing device:

| | |
|---|---|
| Talcum | 5 mg. |
| Magnesium stearate | 5 mg. |
| Corn starch | 9 mg. |

The resulting mixture is then compressed to tablets each weighing 240 mg.

Analoguously tablets are prepared which contain an analgesically active compound of Formula I in an amount of 1 mg/tablet, 2 mg/tablet, 5 mg/tablet, 10 mg/tablet, 25 mg/tablet or 50 mg/tablet.

EXAMPLE II

Suppositories

Suppositories of the following composition are prepared:

| | |
|---|---|
| 1-Methyl-2-benzoyl amino methyl-5-phenyl-1H—2,3-dihydro-1,4-benzo diazepine | 15 mg. |
| Cocoa butter | 1985 mg. |

The active agent and the finely grated suppository material are thoroughly mixed and the mixture is then molten. Suppositories, each weighing 2 g., are cast from the resulting melt which is maintained in homogeneous condition by stirring.

EXAMPLE III

Injectable solution

A formulation which is used for parenteral administration and which has the following composition is produced as follows:

| | |
|---|---|
| 1-Methyl-2-benzoyl amino methyl-5-phenyl 1H—2,3-dihydro-1,4-benzo diazepine | 10% |
| Dimethyl acetamide | 10% |
| Propylene glycol | 50% |
| Benzyl alcohol | 1.5% |
| Ethanol | 10% |
| Water for injection purposes | up to 100% |

The active compound is dissolved in dimethyl acetamide. Benzyl alcohol, propylene glycol, ethanol, and water are then admixed to the solution. The resulting mixture is filtered through a candle filter and filled into suitable ampoules which are sealed and sterilized.

Of course, many changes and variations in the starting materials used, in the reagents employed, in the reaction conditions, temperature, pressure, duration, in the solvents used, in the methods of working up the reaction mixtures and solutions, in purifying the reaction products, in separating the optically active isomers, in producing the acid addition salts, in formulating pharmaceutical preparations containing the novel compounds according to the present invention, and the like may be made by those skilled in the art in accordance with the principles set forth herein and in the claims annexed hereto.

We claim:

1. A 2-phenyl acyl amino methyl-1H-2,3-dihydro-1,4-benzo diazepine compound of the following Formula I

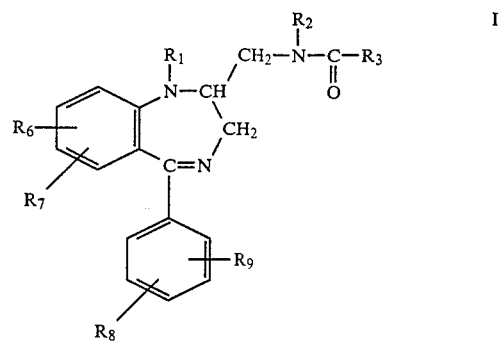

in which $R_1$ indicates a substituent selected from the group consisting of hydrogen, lower alkyl, lower alkenyl, and cyclopropyl methyl;

$R_2$ indicates a substituent selected from the group consisting of hydrogen, lower alkyl, and lower alkenyl;

$R_3$ indicates the group of the following Formula

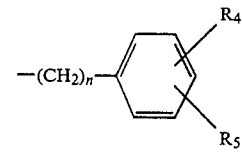

in which $R_4$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino, and lower alkanoyloxy; and $R_5$ indicates a substituent selected from the group consisting of hydrogen, halogen, lower alkyl, lower alkoxy, hydroxyl, and lower alkanoyloxy; with the proviso that one of $R_4$ and $R_5$ indicates a substituent selected from the group consisting of halogen, lower alkyl, nitro and trifluoromethyl;

n indicates a numeral selected from the group consisting of the numerals 0, 1, and 2;

$R_6$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino, and lower alkanoyloxy; and $R_7$ indicates a substituent selected from the group consisting of hydrogen, halogen, lower alkyl, lower alkoxy, hydroxyl, and lower alkanoyloxy; or $R_6$ and $R_7$, when attached to adjacent carbon atoms, together indicate a substituent selected from the group consisting of methylene di-oxy and ethylene di-oxy;

$R_8$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino, and lower alkanoyloxy; and $R_9$ indicates a substituent selected from the group consisting of hydrogen, halogen, lower alkyl, lower alkoxy, hydroxyl, and lower alkanoyloxy; or $R_8$ and $R_9$, when attached to adjacent carbon atoms, together indicate a substituent selected from the group consisting of methylene di-oxy and ethylene di-oxy;

and the optically active isomers of said compounds and their acid addition salts.

2. A 2-phenyl acyl amino methyl-1H-2,3-dihydro-1,4-benzo diazepine compound according to claim 1, in which $R_1$ is a substituent selected from the group consisting of hydrogen, lower alkyl, and cyclopropyl methyl.

3. A 2-phenyl acyl amino methyl-1H-2,3-dihydro-1,4-benzo diazepine compound according to claim 1 or 2, in which the substituent $R_2$ indicates hydrogen.

4. A 2-phenyl acyl amino methyl-1H-2,3-dihydro-1,4-benzo diazepine compound according to claim 1, in which $R_1$ indicates lower alkyl;
$R_2$ indicates hydrogen;
$R_4$ indicates a substituent selected from the group consisting of hydrogen, halogen, cyano, lower alkyl, and lower alkoxy;
$R_5$ indicates a substituent selected from the group consisting of hydrogen, halogen, lower alkyl, and lower alkoxy;
n indicates a numeral selected from the numerals 0, 1, and 2;
$R_6$ indicates a substituent selected from the group consisting of hydrogen, halogen, nitro, lower alkyl, and lower alkoxy;
$R_7$ indicates a substituent selected from the group consisting of hydrogen, halogen, lower alkyl, and lower alkyloxy, and
$R_6$ and $R_7$, when attached to adjacent carbon atoms, together indicate a substituent selected from the group consisting of methylene di-oxy and ethylene di-oxy;
$R_8$ indicates a substituent selected from the group consisting of hydrogen, halogen, lower alkyl, lower alkoxy, and trifluoromethyl; and
$R_9$ indicates a substituent selected from the group consisting of hydrogen, halogen, lower alkyl, and lower alkoxy.

5. A 2-phenylacylaminomethyl-1H-2,3-dihydro-1,4-benzodiazepine compound corresponding to the formula:

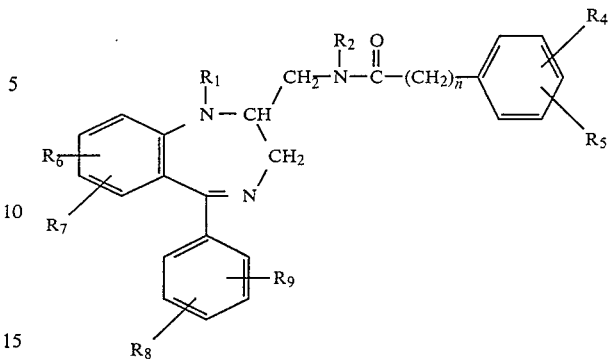

wherein:

$R_1$ indicates a substituent selected from the group consisting of hydrogen, lower alkyl, lower alkenyl, and cyclopropyl methyl;

$R_2$ indicates a substituent selected from the group consisting of hydrogen, lower alkyl, and lower alkenyl;

one of $R_4$ and $R_5$ indicates a cyano substituent and the other of $R_4$ and $R_5$ indicates a substituent selected from the group consisting of hydrogen, halogen, lower alkyl, lower alkoxy, hydroxyl and lower alkanoyloxy;

$R_6$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino and lower alkanoyloxy;

$R_7$ indicates a substituent selected from the group consisting of hydrogen, halogen, lower alkyl, lower alkoxy, hydroxyl and lower alkanoyloxy; or $R_6$ and $R_7$ are attached to adjacent carbon atoms and together indicate a substituent selected from the group consisting of methylene dioxy and ethylene dioxy;

$R_8$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino and lower alkanoyloxy;

$R_9$ indicates a substituent selected from the group consisting of hydrogen, halogen, lower alkyl, lower alkoxy, hydroxyl and lower alkanoyloxy; or $R^8$ and $R^9$ are attached to adjacent carbon atoms and together indicate a substituent selected from the group consisting of methylene dioxy and ethylene dioxy; and n is 0;

and the optically active isomers of said compounds and their acid addition salts.

6. A compound according to claim 5, in which
$R_1$ is methyl;
$R_2$, $R_5$, $R_6$, $R_7$, and $R_8$ are hydrogen;
$R_4$ is cyano;
n is the numeral 0; and
$R_9$ is fluorine;

said compound being 1-methyl-2-(4-cyano benzoyl amino methyl)-5-(2-fluorophenyl)-1H2,3-dihydro-1,4-benzodiazepine, or an acid addition salt thereof.

7. A 2-phenylacylaminomethyl-1H-2,3-dihydro-1,4-benzodiazepine compound corresponding to the formula:

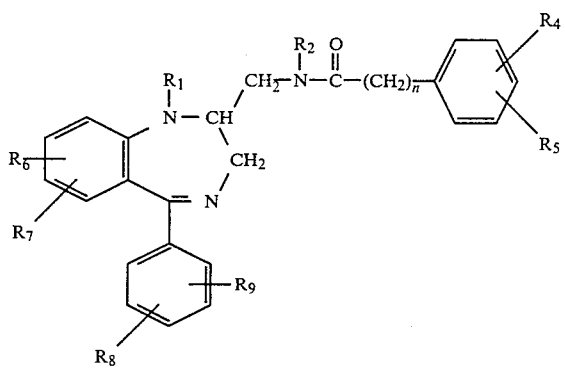

wherein
$R_1$ indicates a lower alkyl substituent;
$R_2$ indicates hydrogen;
$R_4$ indicates a substituent selected from the group consisting of hydrogen, halogen, lower alkyl, lower alkoxy, nitro, and trifluoromethyl;
$R_5$ indicates a substituent selected from the group consisting of hydrogen, halogen, and lower alkyl;
$R_6$ indicates a substituent selected from the group consisting of hydrogen, fluorine and methyl;
$R_7$ indicates hydrogen in the 7-position of the benzodiazepine nucleus, or
$R_6$ and $R_7$ are attached to adjacent carbon atoms and together indicate a substituent selected from the group consisting of methylene dioxy and ethylene dioxy;
$R_8$ indicates a substituent selected from the group consisting of hydrogen, halogen, lower alkyl, lower alkoxy, and trifluoromethyl;
$R_9$ indicates a substituent selected from the group consisting of hydrogen and lower alkyl; and
n indicates a numeral selected from the group consisting of 0 and 1;
and the optically active isomers of said compounds and their acid addition salts.

8. A compound according to claim 7, in which
$R_1$ is methyl;
$R_2$, $R_4$, $R_5$, $R_6$, $R_7$, $R_8$, and $R_9$ are hydrogen; and
n is the numeral 0;
said compound being 1-methyl-2-benzoyl amino methyl-5-phenyl-1H-2,3-dihydro-1,4-benzo diazepine, or an acid addition salt thereof.

9. A compound according to claim 1, in which
$R_1$ is methyl;
$R_2$, $R_4$, $R_5$, $R_7$, $R_8$, and $R_9$ are hydrogen;
n is the numeral 0; and
$R_6$ is fluorine;
said compound being 1-methyl-8-fluoro-2-benzoyl amino methyl-5-phenyl-1H-2,3-dihydro-1,4-benzodiazepine, or an acid addition salt thereof.

10. A compound according to claim 7, in which
$R_1$ is methyl;
$R_4$ is chlorine;
n is the numeral 1;
$R_6$ and $R_7$ together are methylene di-oxy;
$R_8$ is fluorine; and
$R_2$, $R_5$, and $R_9$ are hydrogen;
said compound being 1-methyl-7,8-methylene di-oxy-2-(2-chloro phenacetyl amino methyl)-5-(fluoro phenyl)-1H-2,3-dihydro-1,4-benzodiazepine, or an acid addition salt thereof.

11. A compound according to claim 1, wherein n=0.
12. A compound according to claim 1, wherein one of $R_4$ and $R_5$ is a halogen.
13. A compound according to claim 12, wherein said halogen comprises chlorine or fluorine.
14. A compound according to claim 1, wherein one of $R_4$ and $R_5$ is lower alkyl.
15. A compound according to claim 14, wherein said lower alkyl is methyl.
16. A compound according to claim 1, wherein one of $R_4$ and $R_5$ is nitro.
17. A 2-phenylacylaminomethyl-1H-2,3-dihydro-1,4-benzodiazepine compound corresponding to the formula:

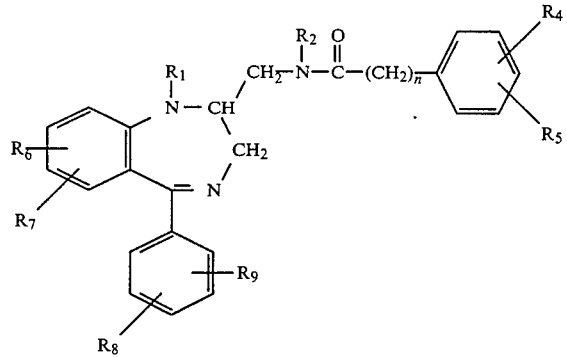

wherein:
$R_1$ indicates a substituent selected from the group consisting of hydrogen and lower alkyl;
$R_2$, $R_4$ and $R_5$ each indicate hydrogen;
one of $R_6$ and $R_7$ indicates a substituent in the 7-position of the benzodiazepine nucleus selected from the group consisting of hydrogen and methyl, and the other of $R_6$ and $R_7$ indicates a substituent selected from the group consisting of hydrogen, halogen, lower alkyl and lower alkoxy, or
$R^6$ and $R_7$ are attached to adjacent carbon atoms and together indicate a substituent selected from the group consisting of methylene dioxy and ethylene dioxy;
$R_8$ indicates a substituent selected from the group consisting of hydrogen, halogen, lower alkyl and trifluoromethyl;
$R_9$ indicates a substituent selected from the group consisting of hydrogen, halogen and lower alkyl, and
n indicates a numeral selected from the group consisting of 0, 1 and 2;
and the optically active isomers of said compounds and their acid addition salts.

18. A compound according to claim 17 wherein n=0 or 1.

19. A compound according to claim 7, wherein
$R_1$ is methyl;
$R_4$ is methoxy;
$R_6$ is methyl;
$R_8$ is fluoro;

$R_2$, $R_5$, $R_7$ and $R_9$ are hydrogen; and n=0, said compound being 1-methyl-8-methyl-2-(4-methoxy benzoylamino methyl)-5-(4-fluoro phenyl)-1H-2,3-dihydro-1,4-benzo diazepine.

20. A compound according to claim 7, wherein $R_1$ is methyl;

$R_4$ is methyl;

$R_6$ is methyl;

$R_8$ is fluoro;

$R_2$, $R_5$, $R_7$ and $R_9$ are hydrogen; and n=0 said compound being 1-methyl-8-methyl-2-(4-methyl benzoyl amino methyl)-5-(4-fluoro phenyl)-1H-2,3-dihydro-1,4-benzo diazepine.

21. A compound according to claim 4, wherein $R_5$ is hydrogen;

n is 0 or 1;

$R_7$ is hydrogen; and $R_9$ is hydrogen.

22. A compound according to claim 21, wherein $R_8$ is hydrogen or halogen.

23. A compound according to claim 21, wherein $R_6$ is substituted at the 8-position of the ring.

24. A compound according to claim 4, wherein $R_7$ is hydrogen;

$R_6$ is hydrogen or a substituent in the 8-position of the ring; and n is 0 or 1.

25. A compound according to claim 21, wherein $R_6$ is hydrogen or a substituent in the 8-position of the ring.

26. A compound according to claim 7, wherein $R_1$ is methyl;

$R_2$, $R_4$, $R_5$, $R_6$ and $R_7$ each are hydrogen;

$R_8$ and $R_9$ are methyl groups substituted at the 2- and 4-positions of the ring; and n=0;

said compound being 1-methyl-2-benzoyl amino methyl-5-(2,4-dimethylphenyl)-1H-2,3-dihydro-1,4-benzodiazepine.

27. In a method of alleviating pain in a mammal, the step of administering to said mammal an effective pain alleviating dose of a 2-phenylacylaminomethyl-1H-2,3-dihydro-1,4-benzodiazepine compound corresponding to the formula:

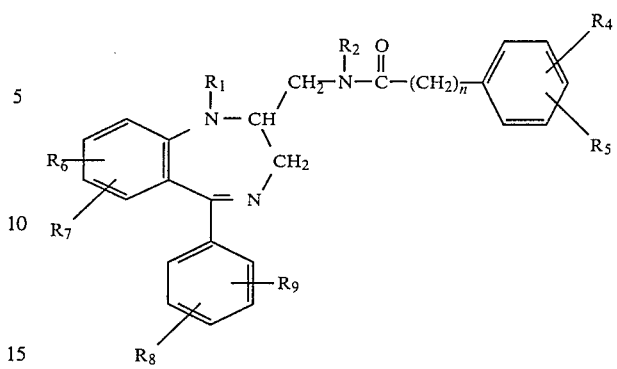

wherein:
$R_1$ indicates a substituent selected from the group consisting of hydrogen, lower alkyl, lower alkenyl and cyclopropyl methyl;
$R_2$ indicates a substituent selected from the group consisting of hydrogen, lower alkyl and lower alkenyl;
$R_4$ indicates a substituent selected from the group consisting of hydrogen, halogen, lower alyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino and lower alkanoyloxy;
$R_5$ indicates a substituent selected from the group consisting of hydrogen, halogen, lower alkyl, lower alkoxy, hydroxyl and lower alkanoyloxy; or
$R_4$ and $R_5$ are attached to adjacent carbon atoms and together indicate a substituent selected from the group consisting of methylene dioxy and ethylene dioxy;
$R_6$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino and lower alkanoyloxy;
$R_7$ indicates a substituent selected from the group consisting of hydrogen, halogen, lower alkyl, lower alkoxy, hydroxyl and lower alkanoyloxy; or
$R_6$ and $R_7$ are attached to adjacent carbon atoms and together indicate a substituent selected from the group consisting of methylene dioxy and ethylene dioxy;
$R_8$ indicates a substituent selected from the group consisting of hydrogen, halogen, lower alkyl, lower alkoxy, hydroxyl, lower alkylthio, nitro, trifluoromethyl, cyano, amino, lower mono-alkyl amino, lower di-alkyl amino, lower mono-alkanoyl amino, lower N-alkyl-N-alkanoyl amino and lower alkanoyloxy;
$R_9$ indicates a substituent selected from the group consisting of hydrogen, halogen, lower alkyl, lower alkoxy, hydroxyl and lower alkanoyloxy; or
$R_8$ and $R_9$ are attached to adjacent carbon atoms and together indicate a substituent selected from the group consisting of methylene dioxy and ethylene dioxy; and n indicates a numeral selected from the group consisting of 0, 1 and 2;
and the optically active isomers of said compounds and their acid addition salts.

28. The method of claim 27, wherein said dose is in a range of from about 0.25 mg. to about 50 mg. for humans.

* * * * *